United States Patent [19]

Inamoto et al.

[11] 4,157,342
[45] Jun. 5, 1979

[54] PROCESS FOR PREPARATION OF 3-ACYLAMINO-4-HOMOISOTWISTANE

[75] Inventors: Yoshiaki Inamoto; Koji Aigami, both of Wakayama, Japan

[73] Assignee: Kao Soap Co., Ltd., Tokyo, Japan

[21] Appl. No.: 917,965

[22] Filed: Jun. 22, 1978

[30] Foreign Application Priority Data

Jul. 6, 1977 [JP] Japan ................... 52-81448

[51] Int. Cl.$^2$ ........................... C07C 103/37
[52] U.S. Cl. ...................... 260/561 R; 260/563 P
[58] Field of Search ..................... 260/561 R

[56] References Cited

U.S. PATENT DOCUMENTS

| 3,670,021 | 6/1972 | Goetz et al. | 260/561 R |
| 3,699,164 | 10/1972 | Fine et al. | 260/561 R X |
| 3,789,074 | 1/1974 | Seale et al. | 260/561 R X |
| 3,855,300 | 12/1974 | Takahashi et al. | 260/561 R X |
| 4,025,568 | 5/1977 | Fujikura et al. | 260/561 R X |

OTHER PUBLICATIONS

Ohsugi et al., Synthesis Comm., 1977, pp. 632-633.
Kock et al., Tet. Letters, 1973, p. 673.
Miller et al., J. Am. Chem. Soc. 95, (1973), p. 5075.
Gewick et al., J. Chem. Soc. Chem. Comm., 1978, p. 738.

*Primary Examiner*—Arthur P. Demers
*Attorney, Agent, or Firm*—Blanchard, Flynn, Thiel, Boutell & Tanis

[57] ABSTRACT

A process for preparing 3-acylamino-4-homoisotwistances which comprises reacting 4-homoisotwistane with a nitrile, bromine and water.

4 Claims, No Drawings

PROCESS FOR PREPARATION OF 3-ACYLAMINO-4-HOMOISOTWISTANE

BACKGROUND OF THE INVENTION FIELD OF THE INVENTION

The present invention relates to a process for the preparation of tricycloundecane derivatives. More particularly, the invention relates to a process for preparing 3-acylamino-4-homoisotwistane (3-acylaminotricyclo[5.3.1.0$^{3.8}$]-undecane) of the following formula (I):

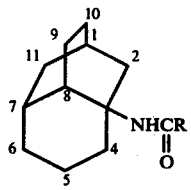

wherein R is alkyl having 1 to 3 carbon atoms, by reacting 4-homoisotwistane (tricyclo[5.3.1.0$^{3.8}$]undecane) of the following formula (II):

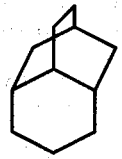

with RCN, wherein R is the same as defined above, in the presence of bromine and water.

The desired product of the present invention, i.e., 3-acylamino-4-homoisotwistane of the formula (I), is very valuable as an intermediate. More specifically, 3-amino-4-homoisotwistane hydrochloride obtained by hydrolyzing the compound of formula (I) of the present invention and neutralizing the hydrolysis product has a high antiviral activity [see Japanese Patent Application No. 93968/75 filed by us and J. Med. Chem., 19, 536 (1976)] and is very valuable as a medicinal component or an active component of an animal medicine.

Some processes for the synthesis of 3-acylamino-4-homoisotwistane of formula (I) have already been disclosed by us. For example, there can be mentioned a process in which 4-homoisotwistane (formula II) is reacted with bromine to form 3-bromo-4-homoisotwistane (IV) (see Japanese Patent Application Laid-Open Specification No. 75052/76) and the compound (IV) is reacted with acetonitrile in the presence of sulfuric acid to form 3-acetylamino-4-homoisotwistane (see Japanese Patent Application No. 62814/75), the reactions of this process being schematically illustrated as follows:

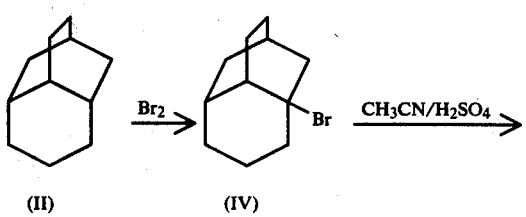

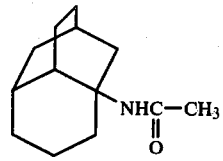

(formula I, R = CH$_3$)

a process in which 4-homoisotwistane (II) is reacted with a nitrile of the following formula (III):

RCN   (III)

wherein R is alkyl having 1 to 3 carbon atoms, in the presence of sulfuric acid and bromine (see Japanese Patent Application No. 145397/76), and a process in which 4-homoisotwistane (II) is reacted with the above-mentioned nitrile (III) and a persulfate in the presence of sulfuric acid (see Japanese Patent Application No. 145396/76).

SUMMARY OF THE INVENTION

We have discovered that when 4-homoisotwistane is reacted with bromine and a nitrile of the above formula (III), in the presence of water, a 3-acylamino-4-homoisotwistane of the above formula (I) can be directly obtained in a high yield without using sulfuric acid. Based on this finding, we have now completed the present invention.

The present invention can be practiced very easily. Namely, the desired product of formula (I) can easily be obtained by agitating a mixture comprising the starting substance (II), the nitrile (III), water and bromine at a predetermined temperature.

The nitrile that is used in the present invention is a compound having the formula (III), and this nitrile (III) includes acetonitrile, propionitrile and butyronitrile. The amount of the nitrile is from 1 to 20 moles, preferably 1 to 10 moles, per one mole of the 4-homoisotwistane, and the amount of water is from 1 to 30 moles, preferably 1 to 20 moles, per one mole of the 4-homoisotwistane. The amount of bromine is from 1 to 10 moles, preferably 1 to 5 moles, per one mole of the 4-homoisotwistane. The reaction temperature is 0 to 70° C., preferably 20° to 50° C.

When the reaction is carried out under the above conditions, the reaction is completed within 48 hours.

The present invention will now be described by reference to the following illustrative, non-limiting Examples of the present invention.

EXAMPLE 1

A mixture of 1 g (6.7 millimoles) of 4-homoisotwistane, 2.4 g (58.5 millimoles) of acetonitrile, 1 g (55.6 millimoles) of water and 5 g (31.3 millimoles) of bromine was agitated for 35 hours at room temperature, and then an aqueous solution of sodium thiosulfate was added to the reaction mixture to remove excess bromine. Then, the reaction mixture was extracted with diethyl ether, and the ether layer was washed with an aqueous solution of sodium bicarbonate and then with water, and then was dried on anhydrous sodium sulfate. Distillation of the ether gave 1.32 g (the yield being 95.6%) of 3-acetylamino-4-homoisotwistane.

Data of various spectra, the melting point and the elementary analysis values of the thus-obtained product are as follows. These data are in agreement with data of the standard substance [see our report on J. Med. Chem., 19, 536 (1976)].

Melting Point: 125° to 126° C.

Elementary Analysis Values: Found: C=75.2%, H=10.1%, N=6.9%: Calculated as $C_{13}H_{21}NO$: C=75.3%, H=10.2%, N=6.7%.

IR (nujol, cm$^{-1}$): 3300, 1640, 1540, 1310, 740.

$^{13}$CNMR (CDCl$_3$, δc): 18.3 (t), 21.3 (t), 24.3 (q), 25.1 (t, d, int.2), 30.4 (t), 31.3 (t), 32.1 (d), 35.6 (d), 36.2 (t), 39.6 (t), 54.3 (s), 169.7 (s).

Mass Spectrum, m/e (relative intensity): 207 (M$^+$ 42), 148 (100), 136 (25), 119 (20), 94 (41), 91 (17), 79 (19), 60 (36), 43 (19).

EXAMPLE 2

A mixture of 1 g (6.7 millimoles) of 4-homoisotwistane, 2.4 g (58.5 millimoles) of acetonitrile, 0.2 g (11.1 millimoles) of water and 3 g (18.8 millimoles) of bromine was agitated for 45 hours at room temperature, and then the reaction mixture was subjected to post treatments in the same manner as described in Example 1 and there was obtained 1.23 g (the yield being 89.1%) of 3-acetylamino-4-homoisotwistane.

The embodiments of the invention in which an exclusive property or privilege is claimed are defined as follows:

1. A process for the preparation of 3-acylamino-4-homoisotwistane having the formula (I):

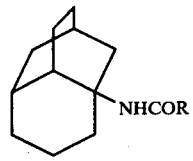
(I)

wherein R is alkyl having 1 to 3 carbon atoms, which consists essentially of reacting 4-homoisotwistane having the formula (II):

(II)

with a nitrile having the formula (III):

RCN   (III)

wherein R is the same as defined above, in the presence of bromine and liquid phase water and in the absence of sulfuric acid, until the formula (I) compound is formed and then recovering the formula (I) compound from the reaction mixture.

2. A process according to claim 1 wherein R is CH$_3$.

3. A process according to claim 1 wherein one mole of 4-homoisotwistane is reacted with from 1 to 20 moles of water, from 1 to 5 moles of bromine and from 1 to 10 moles of said nitrile, at a temperature of from 20° to 50° C.

4. A process according to claim 1 wherein one mole of 4-homoisotwistane is reacted with from 1 to 30 moles of water, from 1 to 10 moles of bromine and from 1 to 20 moles of said nitrile, at a temperature of from 0° to 70° C.

* * * * *